US012561802B2

(12) United States Patent
     Xu et al.

(10) Patent No.: US 12,561,802 B2
(45) Date of Patent: Feb. 24, 2026

(54) ANALYSING ULTRASOUND IMAGE DATA OF THE RECTUS ABDOMINIS MUSCLES

(71) Applicant: KONINKLIJKE PHILIPS N.V., Eindhoven (NL)

(72) Inventors: Jingping Xu, Shanghai (CN); Xiaowei Hong, Shanghai (CN); Zhouye Chen, Shanghai (CN); Yishuang Meng, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 308 days.

(21) Appl. No.: 18/265,016

(22) PCT Filed: Dec. 1, 2021

(86) PCT No.: PCT/EP2021/083822
     § 371 (c)(1),
     (2) Date: Jun. 2, 2023

(87) PCT Pub. No.: WO2022/117674
     PCT Pub. Date: Jun. 9, 2022

(65) Prior Publication Data
     US 2024/0029245 A1     Jan. 25, 2024

(30) Foreign Application Priority Data

Dec. 4, 2020    (WO) ................ PCT/CN2020/133817
Jan. 22, 2021   (EP) ..................................... 21152871

(51) Int. Cl.
     *G06T 7/00*       (2017.01)
     *A61B 8/08*       (2006.01)
     *G06T 7/70*       (2017.01)

(52) U.S. Cl.
     CPC .......... *G06T 7/0012* (2013.01); *A61B 8/0858* (2013.01); *G06T 7/70* (2017.01);
     (Continued)

(58) Field of Classification Search
     CPC ..................... G06T 7/0012; G06T 7/70; G06T 2207/10016; G06T 2207/10132;
     (Continued)

(56) References Cited

U.S. PATENT DOCUMENTS 5,997,479 A    12/1999 Savord et al.
6,013,032 A    1/2000  Powers et al.
     (Continued)

FOREIGN PATENT DOCUMENTS

KR    20190016206 A    2/2019
RU       2692974 C1    6/2019
WO    2020217462 A1   10/2020

OTHER PUBLICATIONS

International Search Report and Written Opinion for PCT/EP2021/083822; Mailing date: Feb. 25, 2022, 9 pages.
     (Continued)

*Primary Examiner* — Siamak Harandi

(57)     ABSTRACT

An apparatus for use in analysing ultrasound image data of rectus abdominis muscles of a subject. The apparatus comprises a memory comprising instruction data representing a set of instructions, and a processor configured to communicate with the memory and to execute the set of instructions. The set of instructions, when executed by the processor, cause the processor to: obtain a sequence of ultrasound image data of the rectus abdominis muscles, the sequence of ultrasound image data having image data having been obtained using an ultrasound transducer tilted at different angles to the surface of the skin of the subject and thus having different angles of ingress of the ultrasound waves into the skin. The processor is further caused to select ultrasound image data from the sequence of ultrasound image data, the selected ultrasound image data comprising image data in the sequence in which a region of the rectus abdominis muscle appears clearest compared to other image
     (Continued)

300

Obtain a sequence of ultrasound image data of the rectus abdominis muscles, the sequence of ultrasound image data having been obtained using an ultrasound transducer tilted at different angles to the surface of the skin of the subject and thus having different angles of ingress of the ultrasound waves into the skin — 302

Select ultrasound image data from the sequence of ultrasound image data, the selected ultrasound image data comprising image data in the sequence in which a region of the rectus abdominis muscle appears clearest compared to other image data in the sequence of ultrasound image data — 304

Make a measurement of the rectus abdominis muscles in the selected ultrasound image data — 306 data in the sequence of ultrasound image data, and make a measurement of the rectus abdominis muscles in the selected ultrasound image data.

20 Claims, 9 Drawing Sheets

(52) U.S. Cl.
CPC .............. *G06T 2207/10016* (2013.01); *G06T 2207/10132* (2013.01); *G06T 2207/20081* (2013.01); *G06T 2207/20101* (2013.01); *G06T 2207/30168* (2013.01)

(58) Field of Classification Search
CPC . G06T 2207/20081; G06T 2207/20101; G06T 2207/30168; A61B 8/0858; A61B 8/5207; A61B 8/5223; A61B 8/08
See application file for complete search history.

(56) References Cited

U.S. PATENT DOCUMENTS

| | | | | |
|---|---|---|---|---|
| 6,283,919 | B1 | 9/2001 | Roundhill et al. | |
| 6,458,083 | B1 | 10/2002 | Jago et al. | |
| 6,530,885 | B1 | 3/2003 | Entrekin et al. | |
| 2015/0325036 | A1* | 11/2015 | Lee ..................... | A61B 5/1101 |
| | | | | 600/437 |
| 2017/0319107 | A1 | 11/2017 | Nguyen | |
| 2021/0128117 | A1* | 5/2021 | Iseri ........................ | A61B 8/14 |

OTHER PUBLICATIONS

Keshwani, N. et al., "Inter-Rectus Distance Measurement Using Ultrasound Imaging: Does the Rater Matter?", Physiother Can., 2016, vol. 68, No. 3, pp. 223-229.

Li, Q. et al., "Continuous thickness measurement of rectus femoris muscle in ultrasound image sequences: A completely automated approach", Biomedical Signal Processing and Control, 2013, vol. 8, Issue 6, pp. 792-798.

Wang, J. et al., "Automatic distance measurement of abdominal aorta for ultrasonographybased visceral fat estimation", 35th Annual International Conference of the IEEE EMBS, Japan, 2013, 4 pages.

Reinpold, W. et al., Classification of rectus diastasis—A proposal by the German Hernia Society (DHG) and the International Endohernia Society (IEHS), Review, 2019, vol. 6, Article 1, 6 pages.

Barbosa, S. et al., "Diastasis of rectus abdominis in the immediate puerperium: correlation between imaging diagnosis and clinical examination", Arch Gynecol Obstet, 2013, vol. 288, pp. 299-303.

Michalska, A. et al., "Diastasis recti abdominis—a review of treatment methods", Ginekologia Polska, 2018, vol. 89, No. 2, pp. 97-101.

Hills, N. et al., "Influence of Ultrasound Transducer Tilt in the Cranial and Caudal Directions on Measurements of Inter-Rectus Distance in Parous Women", Physiotherapy Canada, 2018, vol. 70, No. 1, pp. 6-10.

Kamel. D.M. et al., "Neuromuscular Electrical Stimulation and Strength Recovery of Postnatal Diastasis Recti Abdominis Muscles", Ann Rehabil Med, 2017, vol. 41, No. 3, pp. 465-474.

Liaw, L.J. et al., "The relationships Between Inter-recti Distance Measured by Ultrasound Imaging and Abdominal Muscle Function in Postpartum Women: A 6-Month Follow-up Study", Journal of Orthopaedic & sports physical therapy, 2011, vol. 41, pp. 435-443.

Werner, L.A. et al., "Diastasis Recti Abdominis-Diagnosis, Risk Factors, Effect on Musculoskeletal Function, Framework for Treatment and Implications for the Pelvic Floor", Current Women's Health Reviews, 2018, vol. 14, pp. 1-16.

Salvi, M. et al., "Transverse Muscle Ultrasound Analysis (TRAMA): Robust and Accurate Segmentation of Muscle Cross-Sectional Area", Ultrasound in Med. & Biol., 2019, vol. 45, No. 3, pp. 672-683.

Ecabert, O. et al., "Automatic model-based segmentation of the heart in CT images", IEEE Trans Med Imaging, 2008, vol. 27, No. 9, pp. 1189-1201.

* cited by examiner

300

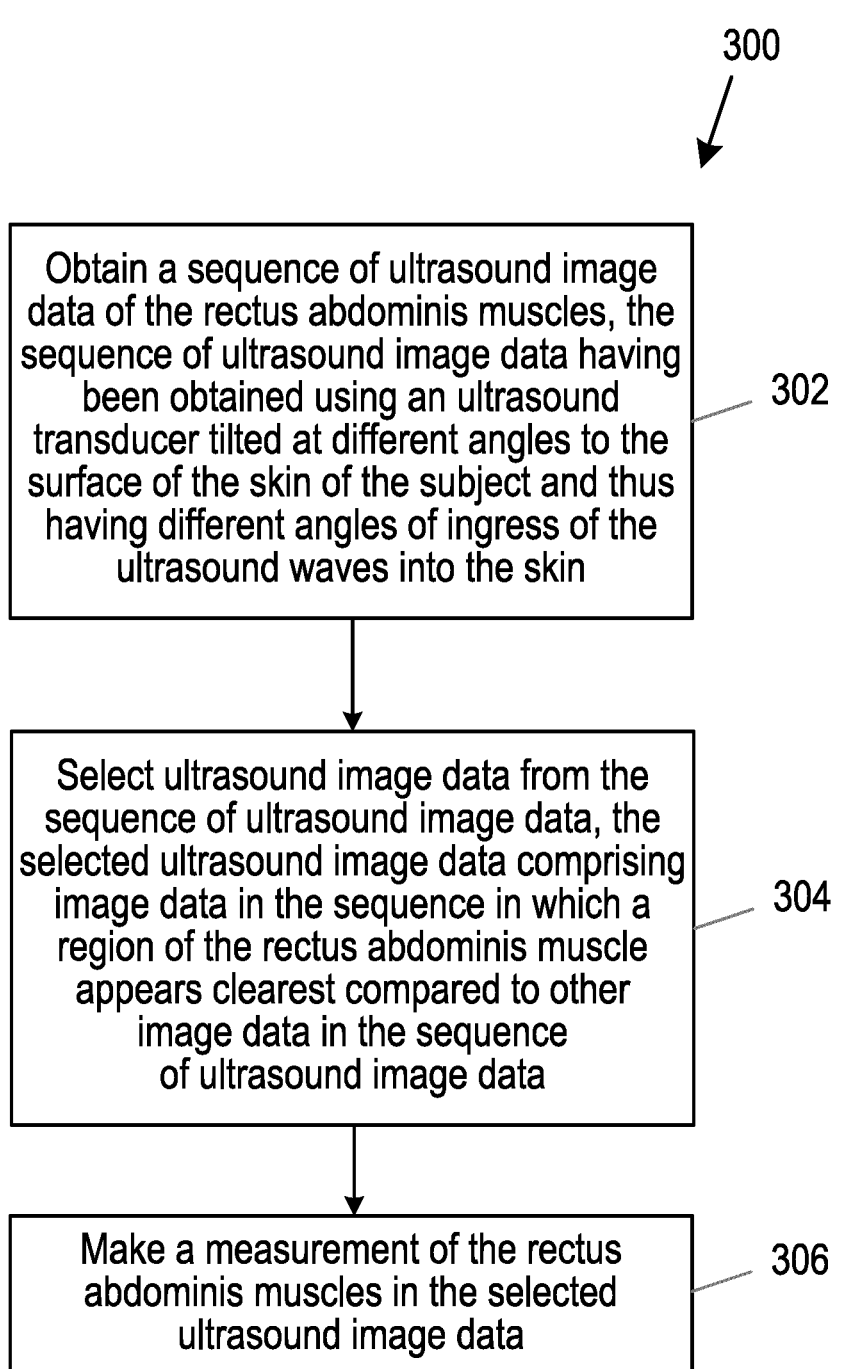

Obtain a sequence of ultrasound image data of the rectus abdominis muscles, the sequence of ultrasound image data having been obtained using an ultrasound transducer tilted at different angles to the surface of the skin of the subject and thus having different angles of ingress of the ultrasound waves into the skin — 302

Select ultrasound image data from the sequence of ultrasound image data, the selected ultrasound image data comprising image data in the sequence in which a region of the rectus abdominis muscle appears clearest compared to other image data in the sequence of ultrasound image data — 304

Make a measurement of the rectus abdominis muscles in the selected ultrasound image data — 306

Fig. 3

Tilting

ANALYSING ULTRASOUND IMAGE DATA OF THE RECTUS ABDOMINIS MUSCLES

CROSS-REFERENCE TO PRIOR APPLICATIONS

This application is the U.S. National Phase application under 35 U.S.C. § 371 of International Application No. PCT/EP2021/083822, filed on Dec. 1, 2021, which claims the benefit of European Patent Application No. 21152871.6, filed on Jan. 22, 2021, and Chinese Patent Application No. PCT/CN2020/133817, filed Dec. 4, 2020. These applications are hereby incorporated by reference herein.

FIELD OF THE INVENTION

The disclosure herein relates to ultrasound systems. Particularly but non-exclusively, the disclosure relates to analysing ultrasound image data of the rectus abdominis muscles of a subject.

BACKGROUND OF THE INVENTION

Abdominal muscles are important spinal stabilizers. Diastasis of the Rectus Abdominis (DRA) also known as Rectus Abdominis Diastasis (RAD) is a condition whereby there is separation of the two rectus abdominis muscles along the Linea Alba (LA), and is commonly associated with postpartum women. RAD is usually diagnosed where there is a separation of more than 2 cm, and a separation of 5 cm or more is considered as severe. RAD can lead to weakness in the abdominal muscles which influences the biomechanical posture causing back pain. RAD has generally been linked with low back pain (LBP), abdominal and pelvic dysfunction (see paper by Wolfgang. R, et. al, entitled '*Classification of rectus diastasis—A proposal by the German Hernia Society (DHG) and the International Endohernia Society (IEHS)*', Frontiers in Surgery, 2019, Vol. 6: Article 1.) The reported prevalence of RAD following pregnancy ranges from 35% to 100%, and women carrying large fetuses or twins to term are particularly susceptible.

The measurement of inter-rectus distance (IRD) is used both to screen for the condition and to monitor treatment. The approaches for measurement of IRD fall into two major groups of 1) physical examination and 2) medical imaging, particularly ultrasound imaging due to its low-cost and real-time capability.

Physical examination can give a rough estimate of the extent of the RAD but it is generally not suitable for monitoring purposes due to lack of measurement precision. Prevalence of mild RAD is high both during pregnancy and after childbirth, and high measurement precision (for example: measurement error of less than 5 mm) is required for longitudinal comparisons during the treatment process.

US 20170319107 A1 disclosed a method of quantifiying distance of the separation between the rectus abdominis muscles from infrared images. RU 0002692974C1 disclosed method for preoperative marking of all intestinal stoma on an anterior abdominal wall of a patient using an ultrasonic visualization.

SUMMARY OF THE INVENTION

As noted above, Rectus Abdominis Diastasis (RAD), is a condition characterised by the separation of the rectus abdominis muscles and is often associated with pregnancy. Physical examination whereby a clinician locates and determines the extent of separation of the stomach muscles with their hands, is generally unsuitable for monitoring purposes due to the subjective nature of examination and the lack of precision of the determined measurements. Regular physical examination in this manner is also undesirable as it can make the muscle separation worse. Physical examination is thus of limited use in monitoring RAD.

Ultrasound is generally considered more suitable for monitoring RAD, however ultrasound imaging requires experienced sonographers and significant investment to train new sonographers to acquire images of sufficient quality that they can be used to monitor RAD. Even when images are obtained, they need to be processed, and this can take time and high levels of experience to obtain reliable results.

It is therefore desirable to provide improved methods and apparatus for processing images of the rectus abdominis, so that measurement results from ultrasound images can be efficiently and accurately processed.

According to a first aspect, there is provided an apparatus for use in analysing ultrasound image data of rectus abdominis muscles of a subject. The apparatus comprises a memory comprising instruction data representing a set of instructions, and a processor configured to communicate with the memory and to execute the set of instructions. The set of instructions, when executed by the processor, cause the processor to: i) obtain a sequence of ultrasound image data of the rectus abdominis muscles, the sequence of ultrasound image data having been obtained using an ultrasound transducer tilted at different angles to the surface of the skin of the subject and thus having different angles of ingress of the ultrasound waves into the skin, ii) select ultrasound image data from the sequence of ultrasound image data, the selected ultrasound image data comprising image data in the sequence in which a region of the rectus abdominis muscle appears clearest compared to other image data in the sequence of ultrasound image data, and iii) make a measurement of the rectus abdominis muscles in the selected ultrasound image data.

According to a second aspect there is an ultrasound imaging system comprising the apparatus of the first aspect, and an ultrasound transducer with which to obtain the sequence of ultrasound image data.

According to a third aspect there is a computer implemented method for use in analysing ultrasound image data of rectus abdominis muscles of a subject. The method comprises i) obtaining a sequence of ultrasound image data of the rectus abdominis muscles, the sequence of ultrasound image data having been obtained using an ultrasound transducer tilted at different angles to the surface of the skin of the subject and thus having different angles of ingress of the ultrasound waves into the skin, ii) selecting ultrasound image data from the sequence of ultrasound image data, the selected ultrasound image data comprising image data in the sequence in which a region of the rectus abdominis muscle appears clearest compared to other image data in the sequence of ultrasound image data; and iii) making a measurement of the rectus abdominis muscles in the selected ultrasound image data.

According to a fourth aspect there is a computer program product comprising computer readable medium the computer readable medium having computer readable code embodied therein, the computer readable code being configured such that, on execution by a suitable computer or processor, the computer or processor is caused to perform the method of the third aspect.

Optimal measurements of the rectus abdominis muscles are generally obtained when the transducer of the probe used to take the ultrasound data is positioned at an angle of 90 degrees to the surface of the targeted organ (e.g. herein the rectus abdominis muscles). In this position, the probe images a slice straight through muscle wall, e.g. along the shortest axis of the muscle. This allows the thickness of the muscle to be accurately determined. As the muscles are not directly visible, the surface of the skin is often used as reference to determine the angle of incidence (so long as the surface is relative flat). Obtaining a 90 degree angle (e.g. to the skin where the skin is used as a reference surface, or more optimally the rectus abdominis muscle) is often difficult for new users, since the inner rectus abdominis structure is under the surface and the ultrasound waves must go through the superficial soft tissue to reach the target rectus abdominis muscles.

The inventors of the disclosure herein have recognised that when the probe is in the correct position, the wall of the muscle (e.g. the outer edge of muscle fibres) appears clearest (e.g. brighter and narrower in a manner akin got optical focus) because the ultrasound waves reflect most strongly and coherently from the muscle boundary when the probe is positioned at 90 degrees. Thus by obtaining ultrasound image data obtained with a probe at a range of angles to the skin surface, and selecting the clearest image data, image data may be selected that provides the most appropriate cross-section through the muscle for making measurements of the muscles such as muscle thickness and muscle separation measurements used to monitor RAD. Measurements of muscle thickness in the selected image are thus more robust and reliable (with better repeatability) and this also avoids the need for the sonographer to independently determine the correct angle of incidence.

These and other aspects will be apparent from and elucidated with reference to the embodiment(s) described hereinafter.

BRIEF DESCRIPTION OF THE DRAWINGS

Example embodiments will now be described, by way of example only, with reference to the following drawings, in which:

FIG. 3 shows an example method according to some embodiments herein;

DETAILED DESCRIPTION OF EMBODIMENTS

As described above, the apparatus and methods described herein allow for improved measurements to be made of the rectus abdominal muscles, for use, for example, in monitoring Rectus Abdominis Diastasis (RAD).

Figure 1:
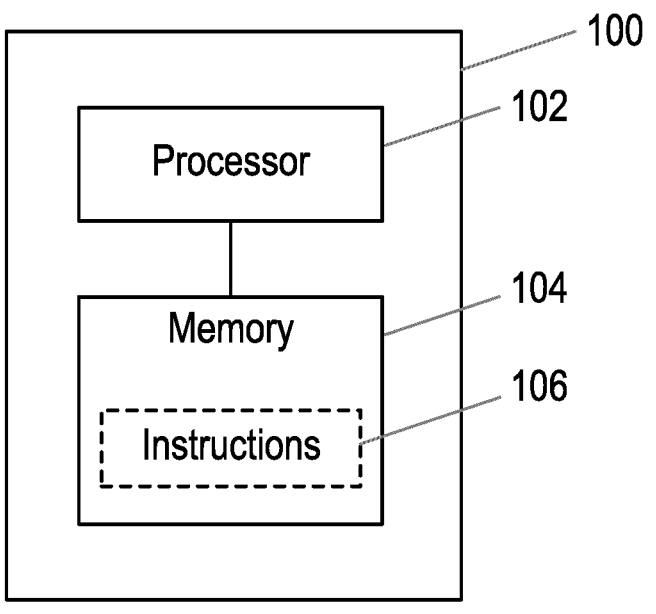
FIG. 1 shows an example apparatus according to some embodiments herein.

Turning now to FIG. 1, which shows an apparatus 100 for use in analysing ultrasound image data of the rectus abdominis muscles of a subject, according to some embodiments herein. Generally, the apparatus may form part of a computer apparatus or system e.g. such as a laptop, desktop computer or other computing device. In some embodiments, the apparatus 100 may form part of a distributed computing arrangement or the cloud.

Generally, the apparatus may be adapted or configured to perform any of the embodiments of the methods described herein, such as the method 300 as described below with respect to FIG. 3.

The apparatus comprises a memory 104 comprising instruction data representing a set of instructions 106 and a processor 102 (e.g. processing circuitry or logic) configured to communicate with the memory and to execute the set of instructions 106. Briefly, the set of instructions 106, when executed by the processor 102, cause the processor 102 to i) obtain a sequence of ultrasound images of the rectus abdominis muscles, the sequence of ultrasound images having been obtained using an ultrasound transducer tilted at different angles to the surface of the skin of the subject and thus having different angles of ingress of the ultrasound waves into the skin, ii) select ultrasound image from the sequence of ultrasound images, the selected ultrasound image comprising image in the sequence in which a region of the rectus abdominis muscle appears clearest compared to other image in the sequence of ultrasound images; and iii) make a measurement of the rectus abdominis muscles in the selected ultrasound image.

As described above, a major problem with conventional 2D ultrasound imaging is operator dependence, which can result in difficulty in monitoring RAD. The proposed apparatus herein guides new users or inexperienced users to obtain the best quality ultrasound image for making measurements of RAD, and then helps them to obtain key parameters with minimum effort. The user merely has to obtain a sequence of ultrasound images at a range of tilts/angles and the apparatus 100 will select an appropriate image in which the muscle boundary is clearest (akin to optical focus) corresponding to the probe being at about 90 degrees to said muscle boundary, within which to make the measurements. The apparatus 100 may thus minimize operator dependence and have a potential role in the assessment of RAD treatment.

In more detail, the processor 102 may comprise one or more processors, processing units, multi-core processors or modules that are configured or programmed to control the apparatus 100 in the manner described herein. In particular implementations, the processor 102 can comprise a plurality of software and/or hardware modules that are each configured to perform, or are for performing, individual or multiple steps of the method described herein. The processor 102 can comprise one or more processors, processing units, multi-core processors and/or modules that are configured or programmed to control the apparatus 100 in the manner described herein. In some implementations, for example, the processor 102 may comprise a plurality of (for example, interoperated) processors, processing units, multi-core processors and/or modules configured for distributed processing. It will be appreciated by a person skilled in the art that such processors, processing units, multi-core processors and/or modules may be located in different locations and may perform different steps and/or different parts of a single step of the method described herein.

The memory 104 is configured to store program code that can be executed by the processor 102 to perform the method described herein. Alternatively or in addition, one or more memories 104 may be external to (i.e. separate to or remote from) the apparatus 100. For example, one or more memories 104 may be part of another device. Memory 104 can be used to store ultrasound image data, the sequence of ultrasound images, and/or any other information or data received, calculated or determined by the processor 102 of the apparatus 100 or from any interfaces, memories or devices that are external to the apparatus 100. The processor 102 may be configured to control the memory 104 to store the ultrasound image data, the sequence of ultrasound images, and/or the any other information or data received, calculated or determined by the processor.

In some embodiments, the memory 104 may comprise a plurality of sub-memories, each sub-memory being capable of storing a piece of instruction data. For example, at least one sub-memory may store instruction data representing at least one instruction of the set of instructions, while at least one other sub-memory may store instruction data representing at least one other instruction of the set of instructions.

It will be appreciated that FIG. 1 only shows the components required to illustrate this aspect of the disclosure and, in a practical implementation, the apparatus 100 may comprise additional components to those shown. For example, the apparatus 100 may further comprise a display. A display may comprise, for example, a computer screen, and/or a screen on a mobile phone or tablet. The apparatus may further comprise a user input device, such as a keyboard, mouse or other input device that enables a user to interact with the apparatus, for example, to provide initial input parameters to be used in the method described herein. The apparatus 100 may comprise a battery or other power supply for powering the apparatus 100 or means for connecting the apparatus 100 to a mains power supply.

In some embodiments, the apparatus 100 may be comprised in an ultrasound system. For example, an ultrasound system may comprise the apparatus 100 described above, and further comprise a transducer with which to record the ultrasound image data and/or the sequence of ultrasound images.

Figure 2:
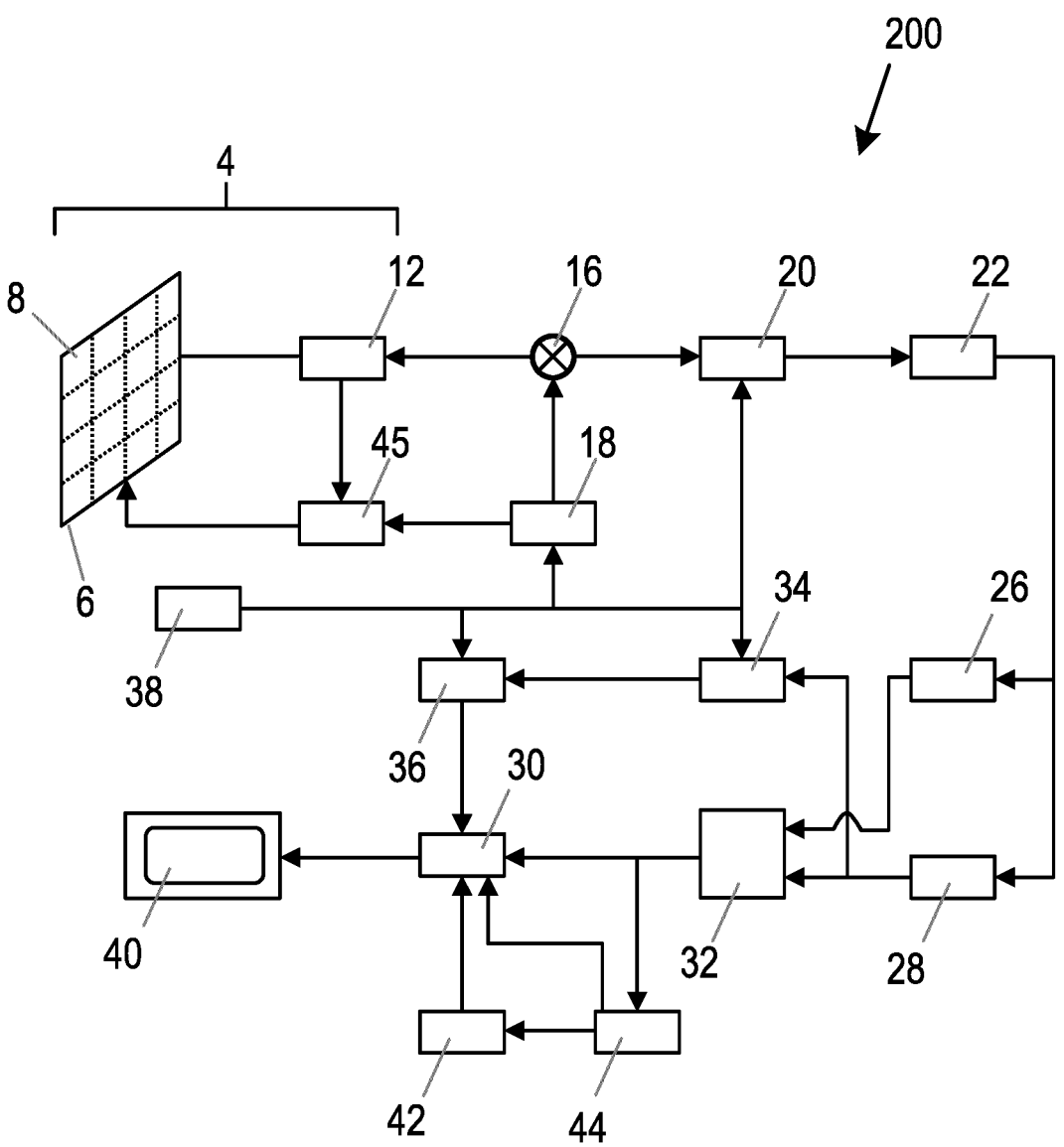
FIG. 2 shows an example ultrasound system according to some embodiments herein.

FIG. 2 shows an example ultrasound system 200. The ultrasound system 200 may comprise the apparatus 100 described above. In other embodiments, components of the ultrasound system 200 may be adapted to perform the method 300 described below.

The system 200 comprises an array transducer probe 4 which has a transducer array 6 for transmitting ultrasound waves and receiving echo information. The transducer array 6 may comprise CMUT transducers; piezoelectric transducers, formed of materials such as PZT or PVDF; or any other suitable transducer technology. In this example, the transducer array 6 is a two-dimensional array of transducers 8 capable of scanning either a 2D plane or a three dimensional volume of a region of interest. In another example, the transducer array may be a 1D array.

The transducer array 6 may be coupled to a microbeamformer 12 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

In an alternative embodiment, instead of a microbeamformer 12, the transducer array may be operated directly by a main system beamformer (not shown in FIG. 2).

The system 200 may further comprise a transmit/receive (T/R) switch 16, which the microbeamformer 12 can be coupled to and which switches the array between transmission and reception modes.

The transmission of ultrasound beams from the transducer array 6 is directed by a transducer controller 18 coupled to the microbeamformer by the T/R switch 16 and a main transmission beamformer (not shown), which can receive input from the user's operation of the user interface or control panel 38. The controller 18 can include transmission circuitry arranged to drive the transducer elements of the array 6 (either directly or via a microbeamformer) during the transmission mode.

It is noted that in an alternative embodiment, where instead of a microbeamformer 12, the transducer array is operated directly by a main system beamformer, a T/R switch 16 may protect the main beamformer 20 from high energy transmit signals.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal represent echoes from structures at increasing depths within the subject.

One of the functions controlled by the transducer controller 18 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered"

imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 18 can be coupled to control a DC bias control 45 for the transducer array. The DC bias control 45 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 12 and are then passed to a main receive beamformer 20 where the partially beamformed signals from individual patches of transducers are combined into a fully beamformed signal, referred to as radio frequency (RF) data. The beamforming performed at each stage may be carried out as described above, or may include additional functions. For example, the main beamformer 20 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 22. The signal processor 22 can process the received echo signals in various ways, such as: band-pass filtering; decimation; I and Q component separation; and harmonic signal separation, which acts to separate linear and nonlinear signals so as to enable the identification of non-linear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 2 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 6 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 26 and a Doppler processor 28. The B mode processor 26 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 28 processes temporally distinct signals arising from tissue movement and blood flow for the detection of moving substances, such as the flow of blood cells in the image field. The Doppler processor 28 typically includes a wall filter with parameters set to pass or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 40. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image is able to depict tissue motion and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. The imaging processor may be adapted to remove certain imaging artifacts from the final ultrasound image, such as for example: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 28 and tissue structure information produced by the B mode processor 26 are coupled to a quantification processor 34. The quantification processor may be used for making measurements in the images. The quantification processor may receive input from a user control panel 38, such as the seed points for locating the surface of the muscle, as described in detail below.

Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 6 and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

The skilled person will appreciate that the detail provided above and the components illustrated in FIG. 2 are an example only and that an ultrasound system may have different components to those illustrated therein.

Turning now back to FIG. 1, and the functionality of the processor 102, as noted above, the processor 102 is caused in step i) to obtain a sequence of ultrasound images of the rectus abdominis muscles, the sequence of ultrasound images having been obtained using an ultrasound transducer tilted at different angles to the surface of the skin of the subject (e.g. patient) and thus having different angles of ingress of the ultrasound waves into the skin. Alternatively or additionally, the processor 102 may obtain ultrasound image data acquired using an ultrasound transducer tilted at different angles to the surface of the skin of the subject. The ultrasound image data may comprise raw ultrasound image data, e.g. RF data obtained by an ultrasound probe, beamformed RF data, etc., as described above with respect to FIG. 2. In some embodiments, the apparatus 100 may be further configured to process such raw ultrasound image data to obtain a sequence of ultrasound images or frames.

In some embodiments, the sequence of ultrasound images may comprise a sequence of ultrasound images or "frames" (e.g. formatted images), such as serial 2D B-mode data frames. In such an example, individual images correspond to a respective angle of ingress of the ultrasound waves into the skin.

The sequence of ultrasound images may be obtained from a database of ultrasound image data, for example, stored in the cloud.

In other embodiments, the apparatus may be configured to obtain the ultrasound image data in (e.g. near) real-time, e.g. from an ultrasound probe. An ultrasound probe may be comprised in the apparatus 100, or separate to (but in communication with) the apparatus 100. As described above, suitable ultrasound probes include, but are not limited to, high-frequency line array transducers. Such a transducer may achieve higher resolution imaging data of the muscles since they are superficial with imaging depth setting to 3~5 cm. In another example a high-frequency linear/curved probe (for example: set at resolution mode) may be used to acquire serial 2D ultrasound image data.

Generally, the sequence of ultrasound images should comprise images having been obtained over the midline of the anterior abdomen towards the pubic symphysis, with the patient in a supine position. In other words, to obtain the sequence of ultrasound images, the sonographer may be instructed to position the transducer in the transverse plane for short-axis views over the midline of the anterior abdomen, on the umbilicus (Um) ring, and scan inferiorly towards the pubic symphysis. Generally the centre of the umbilicus may be used as a reference to ensure good placement of the probe.

The sequence of ultrasound images comprises data obtained using an ultrasound transducer tilted at different angles to the surface of the skin of the subject and thus having different angles of ingress of the ultrasound waves into the skin. The sequence of ultrasound images may comprise image data having been obtained using an ultrasound transducer tilted at different angles spanning a range greater than about −10 degrees to about +10 degrees from the transverse plane; or spanning a range greater than about −20 degrees to about +20 degrees from the transverse plane. Put another way, in one example, the sequence of images may cover angles in the range of 75 degrees to 105 degrees or 85 degrees to 95 degrees (where the probe is defined as being at 90 degrees when it is perpendicular to the skin; as noted above, the objective is to image the muscle wall at a 90 degree angle however, in view that the muscle wall is not visible to the sonographer, the skin is used as a reference surface).

The processor may be configured to instruct a display (e.g. a screen) to provide instructions to a user or sonographer to instruct the user of the manner in which to place the transducer on the subject and the manner in which to move the transducer through an appropriate range of angles in order to obtain an appropriate sequence of images.

Figure 4:
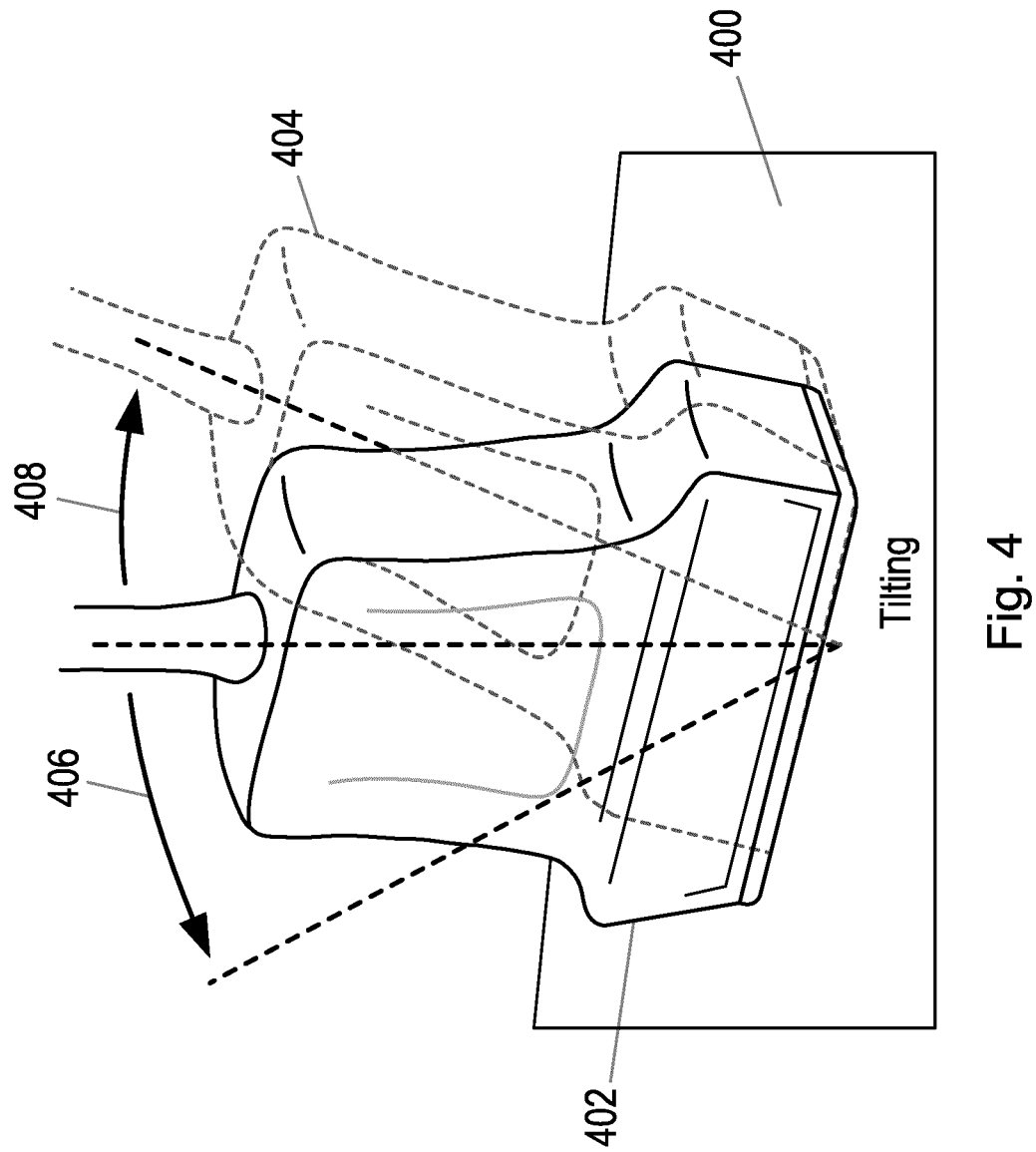
FIG. 4 illustrates an example method of obtaining a sequence of ultrasound image data according to some embodiments herein.

FIG. 4 illustrates an example of how the sequence of ultrasound images may be obtained. In this example, an ultrasound probe is placed on the skin of the subject 400. The probe may be positioned at the umbilical site so as to image the transverse plane through the subject. In this example, the sequence of ultrasound images is then obtained by moving the probe from a tilted position 404, to an upright position 402 (also referred to herein as the probe being at a 90 degree angle to the skin) through to an angle 406. The probe is thus moved through a range of angles 406, 408 about an upright position.

Generally, it is noted that obtaining images across an exact range of angles is not important, rather the objective is to generally obtain ultrasound image data at a range of tilts about a 90 degree angle of ingress into the skin.

Having obtained the sequence of ultrasound images, in step ii), the processor is then caused to select ultrasound image data from the sequence of ultrasound images, the selected ultrasound images comprising the images in the sequence in which a region (e.g. portion) of the rectus abdominis muscle (e.g. muscle fibres) appears clearest compared to other images in the sequence of ultrasound images.

The region of the rectus abdominis may comprise, for example, an outer edge or surface of the rectus abdominis muscle fibres.

As noted above, in order to measure muscle thickness, it is desirable to obtain ultrasound image data when the probe is at (or as close as possible to) 90 degrees to the surface of the rectus abdominis muscle. It has been recognised by the inventors herein that at the 90 degree angle, the outer surface of the rectus abdominis muscle appears clearer compared to other angles. This is because when the ultrasound probe is not at 90 degrees, anisotropy makes the ultrasound image data less clear. The anisotropy of a tissue is related to focal areas of hypo-echogenicity when the ultrasound probe is not at 90 degrees (e.g. not perpendicular to the axis of the structure of interest) to the linear structure being images. Anisotropy is the intrinsic property of some anatomical structures to modify their reflecting capability in respect to the ultrasound beam angle of incidence. If the ultrasound beam does not reflect perpendicularly from linear structures, such as muscles, tendons and ligaments, then reflection is not specular. As such, the returning echoes have low intensity: and the structure incorrectly appears more hypoechoic (the artefact results with a loss of echogenicity in structure). The ability to recognize and correct anisotropy artefacts is important for image quality improvement and optimal patient care. This is particularly noticeable when imaging tendon/muscle. The sonographer can compensate for this by maintaining the 90 degrees angle, however as noted above, this requires high levels of training. By taking a sequence of ultrasound images at different angles of tilt, the image in which the probe was correctly or optimally angled (e.g. close/closest to 90 degrees) may thus be selected as the image frame in which the boundary is clearest. Thus optimal images for muscle measurement may be obtained, without excessive training being required for the sonographer.

The clearest image generally corresponds the image in which the surface of the muscle (e.g. the muscle fibres which appear as the upper/lower boundaries of two separated rectus abdominis muscles) appears brightest and narrowest (sharpest). Thus, in some embodiments the processor 102 may be configured to select the clearest ultrasound image data in the sequence of ultrasound images by determining (and subsequently selecting) the ultrasound image data in which the region of the rectus abdominis muscle (e.g. muscle fibres) appears brightest and/or sharpest compared to other image data in the sequence of ultrasound images. Sharpest in this sense may indicate the ultrasound image data having the highest contrast between muscle boundaries and nearby soft tissue. It may also indicate that the structures appear narrowest (e.g. not "blurred"). Thus, generally, selecting the clearest image data may comprise selecting the image data or frame in which the region of the rectus abdominis is brightest and sharpest (e.g. akin to optical focus) in the selected ultrasound image data.

Figure 5A:
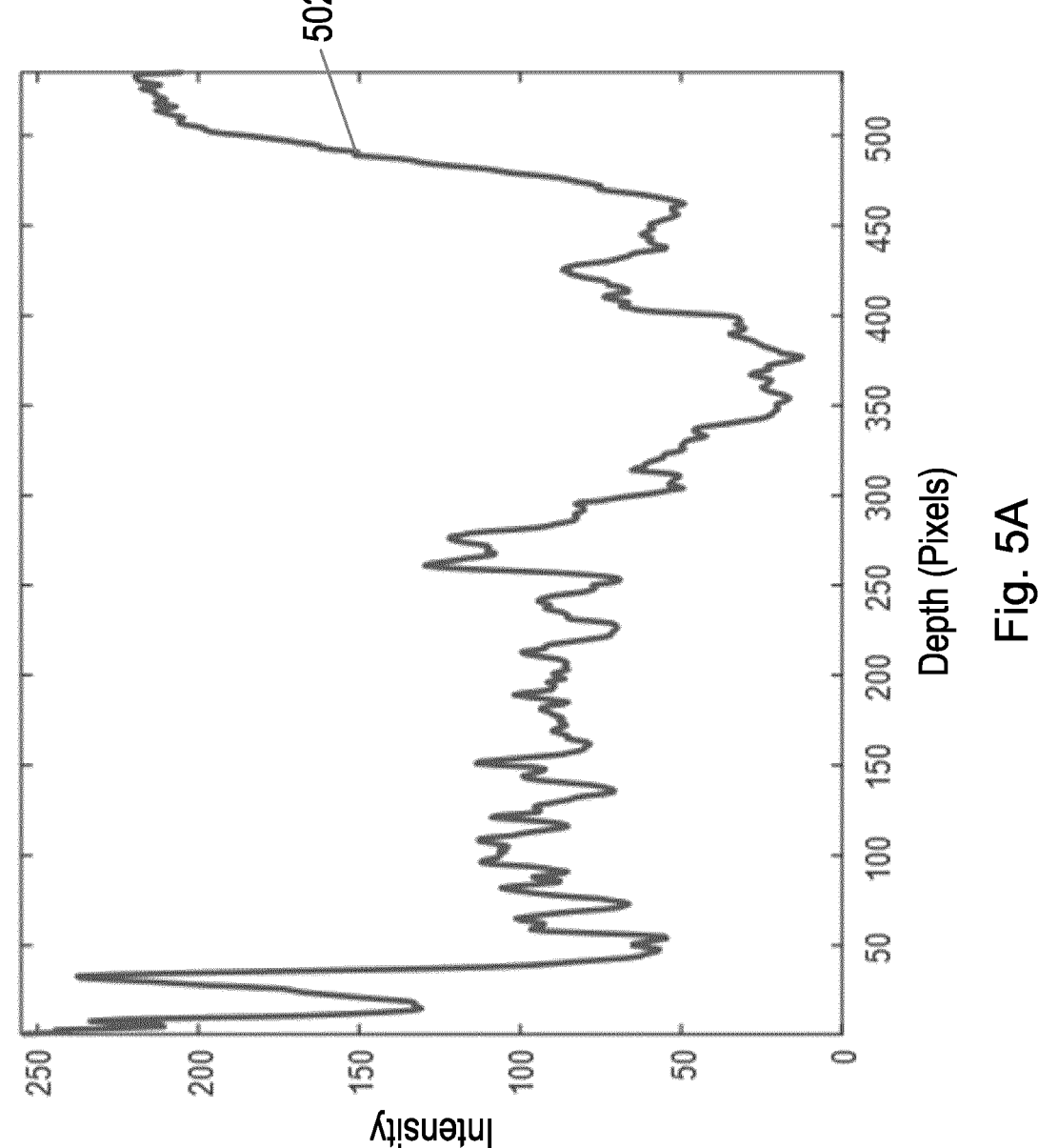
FIG. 5A shows an axial intensity projection curve in an example ultrasound image frame.

The clarity of the images may be assessed in a region or portion of each image data/frame in the sequence of ultrasound images, e.g. a region comprising the muscle boundary. This is illustrated in FIG. 5A which shows the average intensity of an example ultrasound image frame obtained along the lateral direction resulting in an axial intensity projection curve 502. For this example ultrasound image, the minimum value at depth region of [350 to 380] pixels of the projection curve corresponds to the peritoneal cavity (PC). The depth region of [381 to 535] pixels corresponds to imaging artefacts. The depth region of [1 to 50] pixels corresponds to the near field from the ultrasound probe. Thus in this example, a depth region of [51 to 380] pixels may be used for comparing different images in a sequence of ultrasound images.

The clarity of the images may be assessed at the muscle boundary in the image data. For example, the clarity may be assessed for the rectus abdominis muscles (RAM) for muscle fibres which appear as the upper/lower boundaries of two separated RAM (left side and eight side).

In some embodiments, the clarity of the image data is assessed based on the maximum average intensity (e.g. within a region of the image as determined above). Thus, in some embodiments, the processor being caused to select ultrasound image data from the sequence of ultrasound images comprises the processor being caused to select the ultrasound image data having a maximum average intensity.

Figure 5B:
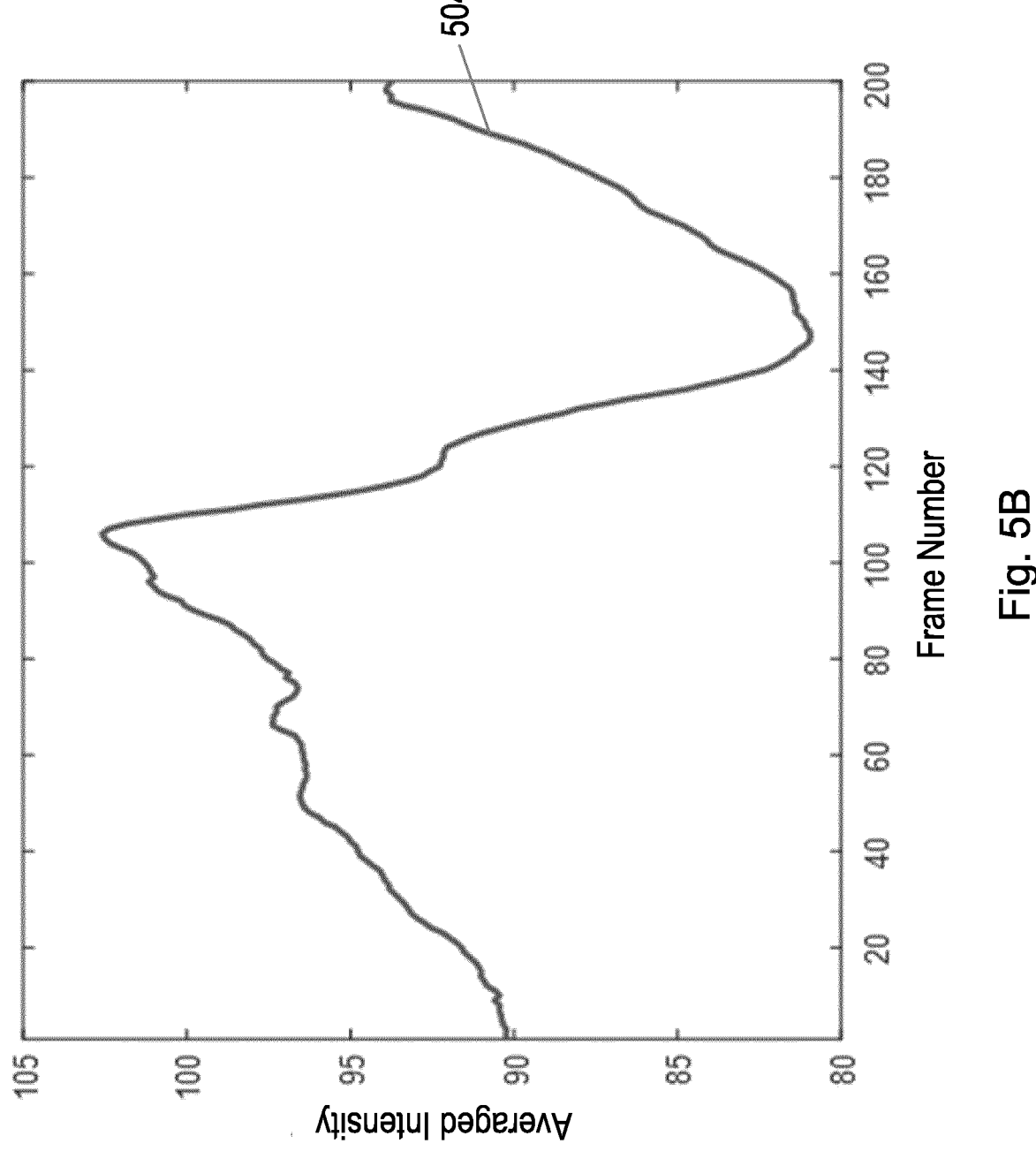
FIG. 5B shows the average intensity of each frame in an example sequence of ultrasound image frames.

An graph showing the average intensity 504 of each frame in an example sequence of ultrasound image frames is plotted in FIG. 5B. The averaged intensity for the selected depth of [51 to 380] pixels and the whole with of [1 to 586] pixels is plotted against frame number as the probe was tilted around 90 degrees at range covering 15~20 degrees. The peak at frame 106th corresponds to ultrasound image data with an angle of ingress closest to 90 degrees to the to the target organ to be examined. In this example, the 106th frame is therefore selected. This illustrates that the muscle boundaries in the ultrasound image data are brighter and narrower if the probe is at the selected optimal frame (the closest to 90 degrees), and broader and fainter if off the selected optimal frame (90 degrees).

In some embodiments, the clarity of the image data is assessed based on the difference in intensity between different images in the sequence (e.g. differences of intensity within a region of each image as described above). Thus, in some embodiments, the processor being caused to select ultrasound image data from the sequence of ultrasound images comprises the processor being additionally or alternatively caused to determine a measure of difference in intensity between neighbouring pairs of images in the sequence of ultrasound images, and select the ultrasound image having a largest measure of difference in intensity. In this example, neighbouring pairs of images may indicate neighbouring pairs of images in a sequence of ultrasound images where the angle of ingress of the ultrasound waves into the skin sequentially increases or decreases between the images in the sequence.

Determining the difference in intensity between neighbouring pairs of images may comprise determining the waveform of the two-dimensional average of adjacent frames, expressed mathematically as: mean2(frame_image $(i+1)$–frame_image(i)) where i is the frame number (from the first to the maximum frame–1). The ultrasound image having the largest measure of difference in intensity may thus correspond to the max-difference peak.

Figure 5C:
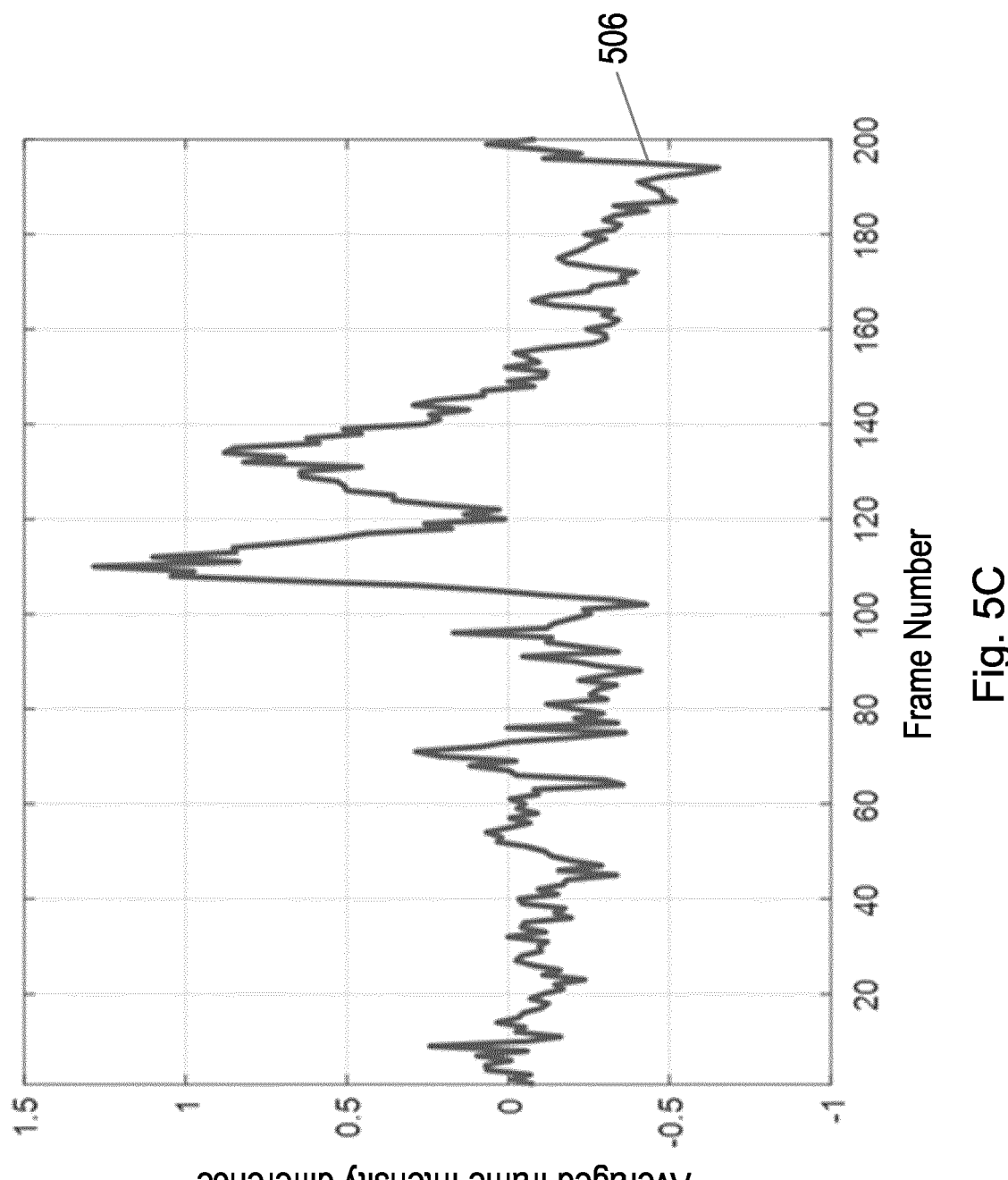
FIG. 5C shows the difference in intensity between neighbouring pairs of images in an example sequence of ultrasound images.

This is illustrated in FIG. 5c which shows the averaged intensity 506 for the selected depth region of [51 to 380] pixels and the whole width of [1 to 586] pixels for the different frames in an example sequence of ultrasound image frames acquired at full tilting from around 90 degrees at range covering a few degrees (for example: 10~15 degrees). The max difference peak is located around 90 degrees at the range of 100th frame to 118th frame, and the best frame corresponds to zero/near zero difference in intensity at frame 106th which corresponds to scanning at 90 degrees. The clearest image frame in this example, is thus determined to be the 106th frame (which is the same result as the result obtained through the maximum intensity approach described above).

In another example, correlation may be used to determine the clearest image in the sequence. For example, additionally or alternatively, the processor being caused to select ultrasound image from the sequence of ultrasound images may comprise the processor being caused to determine a measure of correlation between neighbouring pairs of images in the sequence of ultrasound images, and select the ultrasound image having a largest measure of correlation. This works on the principle that there is highest correlation of the ultrasound waves in images around the 90 degree angle.

Thus in the manner described above, the sequence of ultrasound images may be processed in order to obtain the clearest image corresponding to the ultrasound waves entering the skin/rectus abdominis muscle at approximately 90 degrees, without e.g. extensive training of the sonographer, or through the use of dedicated and costly hardware (accelerometer etc.) to measure the angle.

In some embodiments, the processor may be configured to determine whether suitable ultrasound imaging data (e.g. a suitable frame) for use in making a measurement of the rectus abdominis muscles has been obtained, e.g. whether ultrasound imaging data close enough to the 90 degree angle has been obtained. If not, then the processor may send a message to a display to prompt the user to obtain another sequence of imaging data. This may be repeated until suitable ultrasound imaging data is obtained.

Thus, in one embodiment, the processor is further caused to compare the brightness of the selected ultrasound image data to a threshold brightness. If the brightness is less than the threshold brightness, the processor is further caused to send an instruction to a user display to cause the user display to indicate that a new sequence of ultrasound image data of the rectus abdominis muscles should be obtained. The processor may then be caused to repeat steps i) and ii) for the new sequence of ultrasound image data.

The threshold brightness may be set, for example, based on the maximum intensity that can be obtained based on the settings of the ultrasound machine. For example, the threshold brightness may be set at a percentage of the maximum obtainable brightness. As an example, if the maximum intensity is 255, then the threshold brightness may be set at 200.

In other embodiments, other thresholds may be used to determine whether a suitable sequence of images has been obtained, for example, a threshold coherence level between neighbouring images.

Figure 6:
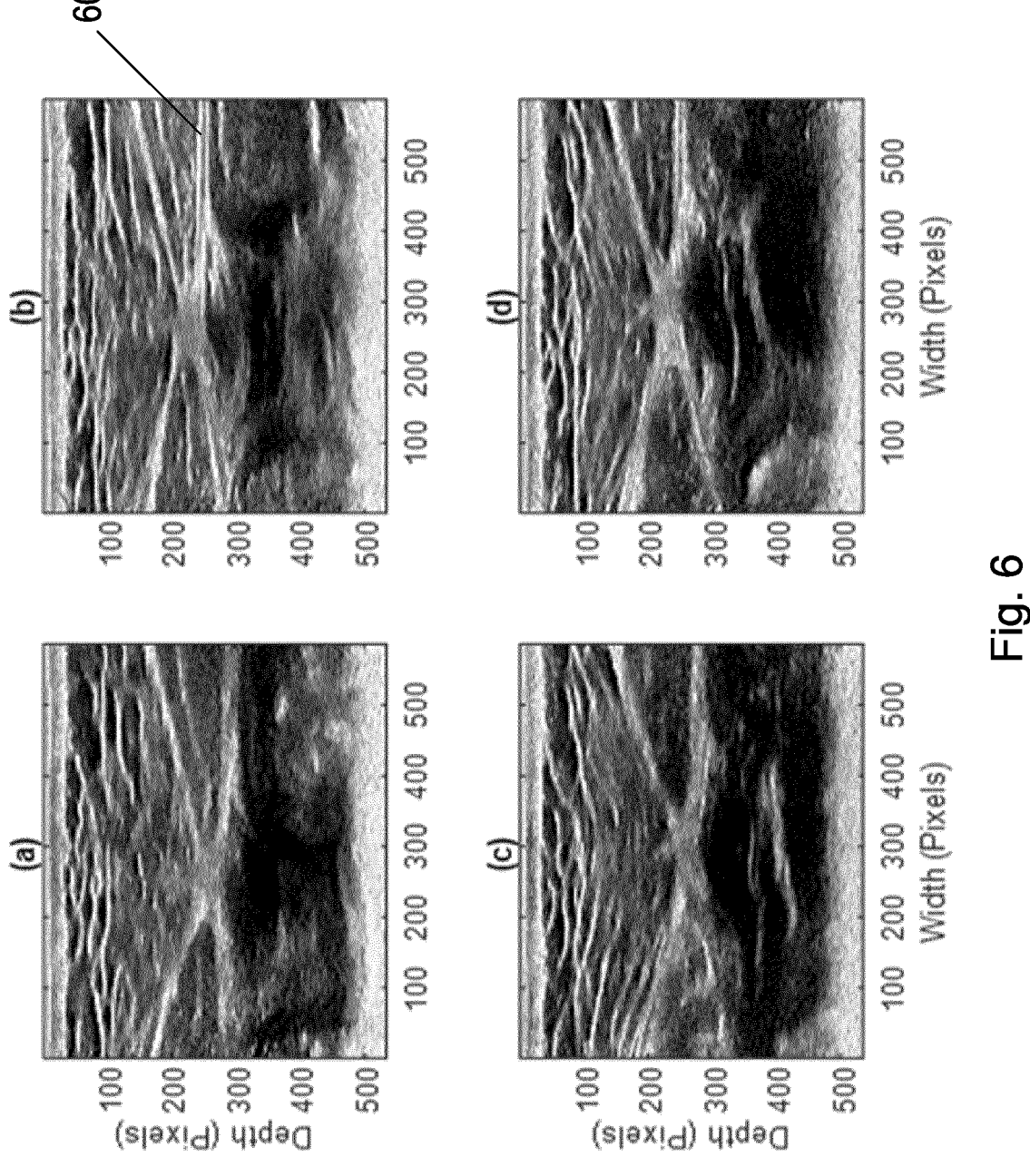
FIG. 6 shows four example two dimensional ultrasound image frames from an example sequence of ultrasound images.

FIG. 6 shows four example two dimensional ultrasound image frames, corresponding to (a) the first frame of the sequence illustrated in FIGS. 5a-c (b) the selected or "best" or optimal" frame, frame number 106 as described above with respect to FIGS. 5a-c (c) frame 147 and frame 200. It can be seen that the boundary of the rectus abdominis 602 (the bright hyperechoic rectus sheath) is clearest (e.g. brightest and narrowest) in FIG. 6b.

In some embodiments, the processor may be caused to prompt a user to obtain two or more sequences of images at different locations on the stomach of the subject/patient. In some examples, the processor may be caused to prompt the user to obtain a sequence of ultrasound imaging data at a) the umbilical site, b) at about 2.5 cm or at about 3 cm above the umbilical ring and c) at about 2.5 cm or at about 3 cm below the umbilical ring. The processor may then be caused to perform steps i) and ii) described above on each of the sequences of ultrasound imaging data to select the clearest ultrasound image data at each site.

Once step ii) has been completed, the processor is caused to iii) make a measurement of the rectus abdominis muscles in the selected ultrasound image data.

This may involve determining the location of the surface of the rectus abdominis muscles in the selected image data. This may be performed in various ways, for example, segmentation (e.g. model based segmentation or machine learning-based segmentation). The skilled person will be familiar with segmentation, but briefly, image segmentation involves extracting shape/form information about the objects or shapes captured in an image. This may be achieved by converting the image into constituent blocks or "segments". In some methods, image segmentation may comprise fitting a model to one or more features in an image.

Examples of segmentation include Model-Based Segmentation (MBS) (see for example, the paper by Ecabert, O., et al. 2008 entitled "Automatic Model-Based Segmentation of the Heart in CT Images"; IEEE Trans. Med. Imaging 27 (9), 1189-1201). Another segmentation method uses machine learning (ML) models to convert an image into a plurality of constituent shapes (e.g. block shapes or block volumes), based on similar pixel/voxel values and image gradients.

In one embodiment, a model-based segmentation may be used to determine the boundary of the rectus abdominis muscle by modelling the rectus abdominis muscles (RAM) in the ultrasound image/data as a hyperbola function (for example: $X^2/a^2 - y^2/b^2 = 1$).

In other embodiments, the surface/boundary of the rectus abdominis muscle may be determined by determining an orientation of each surface in the selected image compared to the surface of the skin. A surface may be selected as the surface of the rectus abdominis based on the determined orientations. For example, it is expected that the surfaces of the two rectus abdominis muscles will slope towards the linea alba (LA) and this may be used to distinguish them from the surface of the skin (which is closer to horizontal. For example, a threshold slope may be used to determine whether a surface identified in the selected ultrasound image data is the surface of the rectus abdominis muscle. As an example, a threshold slope may be set at 12 degrees such that only lines with slopes greater than 12 degrees are classed as corresponding to the surface of the muscle.

If the slope is too small (for example: less than 12 degrees), that means the line structure is near horizontal line which is not consistent with the line structure corresponding to the boundary of the rectus abdominis muscle. If a slope of line structure is over the pre-determined threshold (for example; above 12 degrees) and the length of line structure is long enough (for example: more than ⅓ of the whole imaging width); then the line structure may be classified as corresponding to the boundary of the rectus abdominis muscle.

Figure 7:
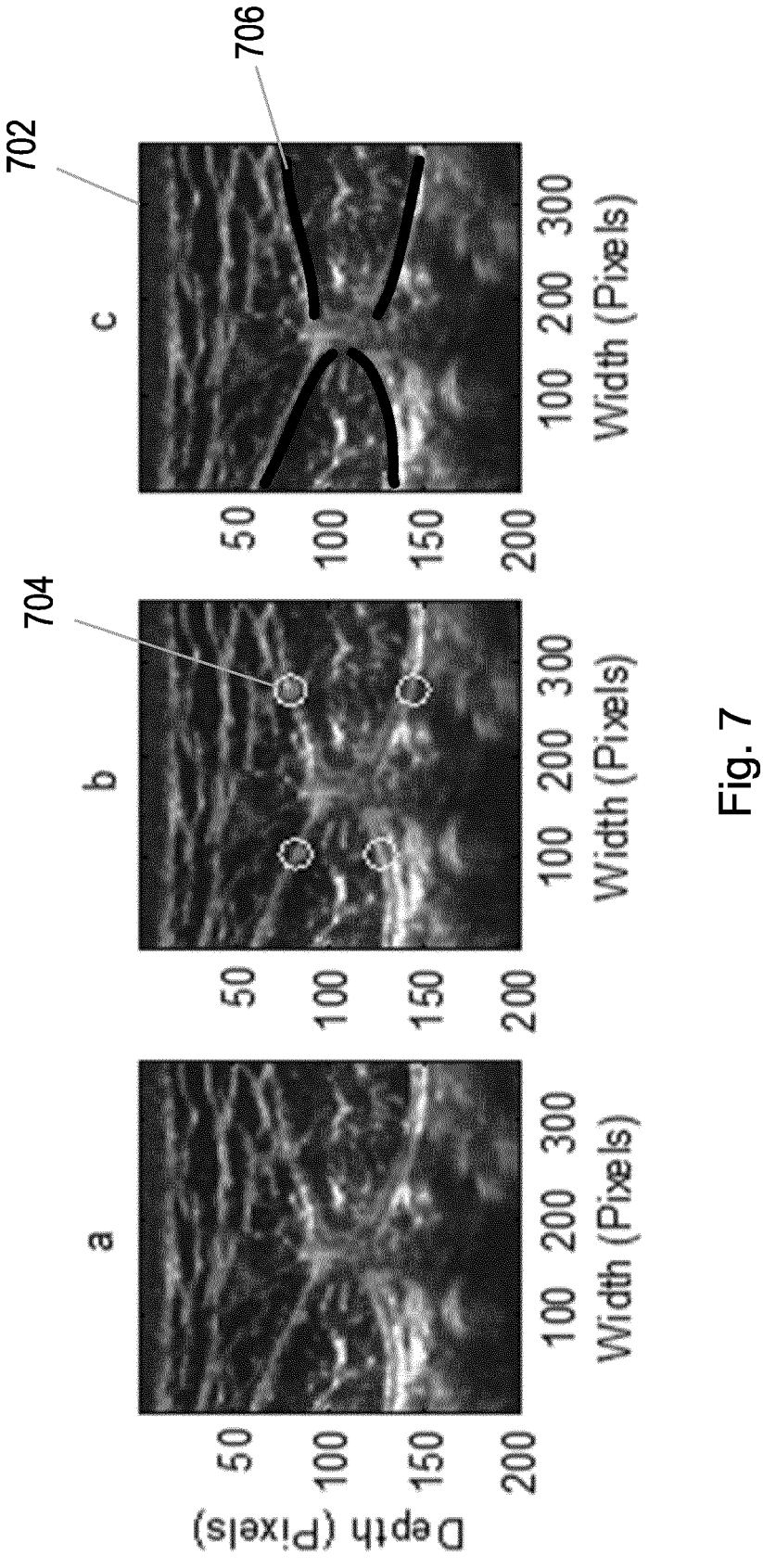
FIG. 7 shows an example selected ultrasound image frame, and illustrates how seed points may be used to determine the boundary of the rectus abdominis.

In a further embodiment, one or more user-input locations on the surface of the rectus abdominis may be used as seed points to trace the surface of the rectus abdominis in the selected image data. The skilled person will be familiar with methods of using seed points to trace (e.g. determine the location of) a line in an image. This is illustrated in FIG. 7 which shows an example selected ultrasound image frame 702 in FIG. 7a, example seed points 704 as indicated by a user (e.g. using a user input device) and the determined location of the boundary of the rectus abdominis muscle 706. In this example, it is noted that the LA is located within depth range of [85 120] pixels, and width range of [150 200] pixels, the boundaries of both rectus abdominis muscles are clearly visible at a depth range of [60 160] pixels. The four user selected seed points 704 in this example are at [82 102], [128 102], [79 273], [144 273]. The seed points are used as initial points for boundary searching. The IRD and muscle thickness may be determined from FIG. 7c.

In another embodiment, a model trained using a machine learning process may be used to predict the location of the surface of the rectus abdominis muscles. Such a model may be trained on training data comprising ultrasound images of rectus abdominis muscles where the surface is correctly labelled, e.g. by a human expert. As an example, a convolutional neural network may be trained to perform such a task based on a training dataset (e.g. using back propagation/gradient descent). The skilled person will be familiar with methods of training a machine learning model to label images and will appreciate that a convolutional neural network is merely an example and that wide range of different models may be trained for such a task.

Once the muscle boundaries have been determined then the method may be caused to perform step iii) and make a measurement of the rectus abdominis muscles in the selected ultrasound image data. The measurement of the rectus abdominis muscles may comprise a measure of muscle thickness and/or a measure of separation of the rectus abdominis muscles. As noted above, the measurement may be for use in monitoring diastasis recti in the subject.

Thus, in this manner, RAD may be effectively monitored in a patient, using ultrasound imaging, without the need for extensive training of the sonographer in order to obtain suitable image data.

Turning to FIG. 3, there is a computer implemented method 300 for use in analysing ultrasound image data of rectus abdominis muscles of a subject. Embodiments of the method 300 may be performed, for example by an apparatus such as the apparatus 100 or the ultrasound system 200 described above.

Briefly, in a first step 302 the method comprises obtaining a sequence of ultrasound image data of the rectus abdominis muscles, the sequence of ultrasound image data having been obtained using an ultrasound transducer tilted at different angles to the surface of the skin of the subject and thus having different angles of ingress of the ultrasound waves into the skin. Obtaining a sequence of ultrasound image data was described in detail above with respect to the apparatus 100 and the detail therein will be understood to apply equally to the method 300.

In a second step 304 the method comprises selecting ultrasound image from the sequence of ultrasound images, the selected ultrasound image comprising image in the sequence in which a region of the rectus abdominis muscle appears clearest compared to other image in the sequence of ultrasound images. Selecting the clearest ultrasound image from the sequence of ultrasound images was described in detail above with respect to the apparatus 100 and the detail therein will be understood to apply equally to the method 300.

In a third step 306, the method comprises making a measurement of the rectus abdominis muscles in the selected ultrasound image. Making a measurement of the rectus abdominis muscles was described in detail above with respect to the apparatus 100 and the detail therein will be understood to apply equally to the method 300.

There is thus provided a method of making measurements of the rectus abdominis muscles to better facilitate monitoring of diastasis of the rectus abdominis.

In another embodiment, there is provided a computer program product comprising a computer readable medium, the computer readable medium having computer readable code embodied therein, the computer readable code being configured such that, on execution by a suitable computer or processor, the computer or processor is caused to perform the method or methods described herein.

Thus, it will be appreciated that the disclosure also applies to computer programs, particularly computer programs on or in a carrier, adapted to put embodiments into practice. The program may be in the form of a source code, an object code, a code intermediate source and an object code such as in a partially compiled form, or in any other form suitable for use in the implementation of the method according to the embodiments described herein.

It will also be appreciated that such a program may have many different architectural designs. For example, a program code implementing the functionality of the method or system may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for monitoring diastasis of rectus abdominis muscles of a subject, the apparatus comprising:
a memory comprising instruction data representing a set of instructions; and
a processor configured to communicate with the memory and to execute the set of instructions, wherein the set of instructions, when executed by the processor, cause the processor to:
obtain a sequence of ultrasound images of the rectus abdominis muscles from an ultrasound system, the sequence of ultrasound images having been obtained using an ultrasound transducer of the ultrasound system tilted at different angles to a surface of skin of the subject and thus having different angles of ingress of ultrasound waves into the skin;
select an ultrasound image from the sequence of ultrasound images, the selected ultrasound image comprising an image in the sequence in which a region of the rectus abdominis muscles appears clearest compared to other images in the sequence of ultrasound images; and make a measurement of the rectus abdominis muscles comprising locating a surface of the rectus abdominis muscles in image data automatically extracted from the selected ultrasound image.

2. The apparatus as in claim 1, wherein the processor being caused to select the ultrasound image from the sequence of ultrasound images comprises the processor being caused to:
select the ultrasound image in which the region of the rectus abdominis muscles appears brightest compared to other images in the sequence of ultrasound images.

3. The apparatus as in claim 1, wherein the processor is further caused to compare brightness of the selected ultrasound image to a threshold brightness; and
when the brightness is less than the threshold brightness, send an instruction to a user display to cause the user display to indicate that a new sequence of ultrasound images of the rectus abdominis muscles should be obtained; and
repeat selecting another ultrasound image for the new sequence of ultrasound images, making a measurement of the rectus abdominis muscles in the selected another ultrasound image.

4. The apparatus as in claim 1, wherein the processor being caused to select the ultrasound image from the sequence of ultrasound images comprises the processor being caused to:
select the ultrasound image in which the region of the rectus abdominis muscles appears sharpest compared to other images in the sequence of ultrasound images.

5. The apparatus as in claim 1, wherein the processor being caused to select the ultrasound image from the sequence of ultrasound images comprises the processor being caused to:
select the ultrasound image having a maximum average intensity.

6. The apparatus as in claim 1, wherein the processor being caused to select the ultrasound image from the sequence of ultrasound images comprises the processor being caused to:
determine a measure of difference in intensity between neighbouring pairs of images in the sequence of ultrasound images; and
select the ultrasound image having a largest measure of difference in intensity.

7. The apparatus as in claim 1, wherein the processor (being caused to the select ultrasound image from the sequence of ultrasound images comprises the processor being caused to:
determine a measure of correlation between neighbouring pairs of images in the sequence of ultrasound images; and
select the ultrasound image having a largest measure of correlation.

8. The apparatus as in claim 1, wherein the sequence of ultrasound images comprises images having been obtained over a midline of an anterior abdomen towards a pubic symphysis.

9. The apparatus as in claim 1, wherein said different angles comprise different angles spanning a range greater than about −10 degrees to about +10 degrees from a transverse plane; or spanning a range greater than about −20 degrees to about +20 degrees from the transverse plane.

10. The apparatus as in claim 1 wherein the measurement of the rectus abdominis muscles comprises a measure of muscle thickness and/or a measure of separation of the rectus abdominis muscles.

11. The apparatus as in claim 10, wherein the measurement is for use in monitoring diastasis recti in the subject.

12. An ultrasound imaging system comprising the apparatus of claim 1 and the ultrasound transducer with which to obtain the sequence of ultrasound images.

13. A computer implemented method for use in analyzing ultrasound image data of rectus abdominis muscles of a subject, the method comprising:

obtaining a sequence of ultrasound images of the rectus abdominis muscles, the sequence of ultrasound images having been obtained using an ultrasound transducer tilted at different angles to a surface of skin of the subject and thus having different angles of ingress of ultrasound waves into the skin;

selecting an ultrasound image from the sequence of ultrasound images, the selected ultrasound image comprising an image in the sequence in which a region of the rectus abdominis muscles appears clearest compared to other images in the sequence of ultrasound images; and making a measurement of the rectus abdominis muscles in the selected ultrasound image, wherein making the measurement of the rectus abdominis muscles comprises locating a surface of the rectus abdominis muscles in the selected image by:

segmentation;

determining an orientation of each surface in the selected image compared to the surface of the skin, and selecting a surface as the surface of the rectus abdominis muscles based on the determined orientations;

using one or more user-input locations on the surface of the rectus abdominis muscles as seed points to trace the surface of the rectus abdominis muscles in the selected image; and/or using a model trained using a machine learning process to predict the location of the surface of the rectus abdominis muscles.

14. An apparatus for use in analyzing ultrasound image data of rectus abdominis muscles of a subject, the apparatus comprising:

a memory comprising instruction data representing a set of instructions; and a processor configured to communicate with the memory and to execute the set of instructions, wherein the set of instructions, when executed by the processor, cause the processor to:

obtain a sequence of ultrasound images of the rectus abdominis muscles, the sequence of ultrasound images having been obtained using an ultrasound transducer tilted at different angles to a surface of skin of the subject and thus having different angles of ingress of ultrasound waves into the skin;

select an ultrasound image from the sequence of ultrasound images, the selected ultrasound image comprising an image in the sequence in which a region of the rectus abdominis muscles appears clearest compared to other images in the sequence of ultrasound images; and make a measurement of the rectus abdominis muscles in the selected ultrasound image wherein making the measurement of the rectus abdominis muscles comprises locating a surface of the rectus abdominis muscles in the selected image by:

segmentation;

20 determining an orientation of each surface in the selected image compared to the surface of the skin, and selecting a surface as the surface of the rectus abdominis muscles based on the determined orientations;

using one or more user-input locations on the surface of the rectus abdominis muscles as seed points to trace the surface of the rectus abdominis muscles in the selected image; and/or using a model trained using a machine learning process to predict the location of the surface of the rectus abdominis muscles.

15. The apparatus as in claim 14, wherein the processor being caused to select the ultrasound image from the sequence of ultrasound images comprises the processor being caused to:

select the ultrasound image in which the region of the rectus abdominis muscles appears brightest compared to other images in the sequence of ultrasound images.

16. The apparatus as in claim 14, wherein the processor is further caused to compare brightness of the selected ultrasound image to a threshold brightness; and when the brightness is less than the threshold brightness, send an instruction to a user display to cause the user display to indicate that a new sequence of ultrasound images of the rectus abdominis muscles should be obtained; and repeat selecting another ultrasound image for the new sequence of ultrasound images, making a measurement of the rectus abdominis muscles in the selected another ultrasound image.

17. The apparatus as in claim 14, wherein the processor being caused to select the ultrasound image from the sequence of ultrasound images comprises the processor being caused to:

select the ultrasound image in which the region of the rectus abdominis muscles appears sharpest compared to other images in the sequence of ultrasound images, or select the ultrasound image having a maximum average intensity.

18. The apparatus as in claim 14, wherein the processor being caused to select the ultrasound image from the sequence of ultrasound images comprises the processor being caused to:

determine a measure of difference in intensity between neighbouring pairs of images in the sequence of ultrasound images; and select the ultrasound image having a largest measure of difference in intensity.

19. The apparatus as in claim 14, wherein the processor being caused to select the ultrasound image from the sequence of ultrasound images comprises the processor being caused to:

determine a measure of correlation between neighbouring pairs of images in the sequence of ultrasound images; and select the ultrasound image having a largest measure of correlation.

20. The apparatus as in claim 14, wherein the sequence of ultrasound images comprises images having been obtained over a midline of an anterior abdomen towards a pubic symphysis.

* * * * *